(12) United States Patent
Denove et al.

(10) Patent No.: US 12,232,761 B2
(45) Date of Patent: Feb. 25, 2025

(54) ROTARY SURGICAL SHAVER

(71) Applicant: Arthrex, Inc., Naples, FL (US)

(72) Inventors: Peter Denove, Naples, FL (US);
Andrew Hsu, Anaheim, CA (US);
Kenneth M. Adams, Naples, FL (US)

(73) Assignee: Arthrex, Inc., Naples, FL (US)

( * ) Notice: Subject to any disclaimer, the term of this patent is extended or adjusted under 35 U.S.C. 154(b) by 828 days.

(21) Appl. No.: 17/391,626

(22) Filed: Aug. 2, 2021

(65) Prior Publication Data
US 2021/0353327 A1    Nov. 18, 2021

Related U.S. Application Data

(63) Continuation of application No. 16/296,997, filed on Mar. 8, 2019, now Pat. No. 11,083,486.

(51) Int. Cl.
*A61B 17/3207* (2006.01)
*A61B 17/32* (2006.01)

(52) U.S. Cl.
CPC ........... *A61B 17/320758* (2013.01); *A61B 17/32002* (2013.01); *A61B 2017/320032* (2013.01)

(58) Field of Classification Search
CPC ...... A61B 17/320016; A61B 17/32002; A61B 2017/320032; A61B 2017/32006; A61B 17/320758
See application file for complete search history.

(56) References Cited

U.S. PATENT DOCUMENTS

| | | | |
|---|---|---|---|
| 1,493,240 A | 5/1924 | Bohn | |
| 4,203,444 A | 5/1980 | Bonnell et al. | |
| 4,285,618 A | 8/1981 | Shanley | |
| 4,983,179 A | 1/1991 | Sjostrom | |
| 5,676,321 A | 10/1997 | Kroger | |
| 5,913,867 A | 6/1999 | Dion | |
| 6,053,923 A | 4/2000 | Veca et al. | |
| 7,485,125 B2 | 2/2009 | Sjostrom | |
| 7,572,259 B2 | 8/2009 | Desarzens et al. | |
| 7,621,915 B2 | 11/2009 | Frederick et al. | |

(Continued)

FOREIGN PATENT DOCUMENTS

| | | |
|---|---|---|
| DE | 102007034087 | 9/2009 |
| GB | 2093353 | 9/1984 |
| WO | 0249518 | 3/2003 |

OTHER PUBLICATIONS

Boston University, "Projects—Current Projects," Boston University, bu.edu, Dec. 12, 2009, 2 pages.

(Continued)

*Primary Examiner* — Larry E Waggle, Jr.
(74) *Attorney, Agent, or Firm* — Greenberg Traurig, P.A.; Michael K. Dixon

(57) ABSTRACT

A handheld rotary medical device with a shaver configured to remove cartilage is disclosed. The handheld rotary medical device may include an inner drive shaft, an elongated, tubular, outer housing encapsulating the inner drive shaft such that the inner drive shaft is positioned within the outer housing and a shaver at a distal end of the inner drive shaft. The shaver may include a plurality of teeth extending radially outward from an outer surface of the inner drive shaft. The medical device may include slots or grooves in the outer housing useful for cleaning the tissue from the teeth of the shaver.

20 Claims, 3 Drawing Sheets

(56) References Cited

U.S. PATENT DOCUMENTS

| | | |
|---|---|---|
| 7,850,691 B2 | 12/2010 | Lechot |
| 7,922,720 B2 | 4/2011 | May et al. |
| 8,414,606 B2 | 4/2013 | Shadeck et al. |
| 8,475,483 B2 | 7/2013 | Schmitz et al. |
| 8,632,561 B2 | 1/2014 | Seipel et al. |
| 8,814,871 B2 | 8/2014 | Mansmann |
| 9,232,953 B2 | 1/2016 | Bono et al. |
| 9,861,380 B2 | 1/2018 | Hart et al. |
| 9,907,564 B2 | 3/2018 | Lockard et al. |
| 10,028,767 B2 | 7/2018 | Germain et al. |
| 11,083,486 B2 * | 8/2021 | Denove .......... A61B 17/320758 |
| 2005/0137600 A1 | 6/2005 | Jacobs et al. |
| 2010/0030216 A1 | 2/2010 | Arcenio |
| 2013/0072936 A1 | 3/2013 | To et al. |
| 2013/0103067 A1 | 4/2013 | Fabro et al. |
| 2013/0110145 A1 | 5/2013 | Weitzman |
| 2013/0211408 A1 * | 8/2013 | Kather ................ A61B 17/1617 606/83 |
| 2017/0057103 A1 | 3/2017 | Perlberg et al. |
| 2018/0085139 A1 | 3/2018 | Hart et al. |
| 2019/0223898 A1 | 7/2019 | Curtin et al. |
| 2019/0239912 A1 * | 8/2019 | Schlottman ...... A61B 17/32002 |

OTHER PUBLICATIONS

University of South Florida, "Design of a Minimally Invasive Laparoscopic Tissue Removal Device," usf.edu, Tech ID # 12B160, 2018, 1 page.

\* cited by examiner

ROTARY SURGICAL SHAVER

CROSS-REFERENCE TO RELATED APPLICATION

This application is a continuation of U.S. Provisional patent application Ser. No. 16/296,997, filed on Mar. 8, 2019, which is incorporated herein in its entirety.

BACKGROUND

Handheld rotary medical devices typically include detachable working ends, which are often shavers or burrs that are configured for the removal of hard or soft tissue from the body. The detachable working ends are typically attached to the handheld devices via any one of numerous releasable connection systems. Many of these devices are configured to remove soft tissue and are unable to efficiently and effectively remove joint cartilage in a body.

SUMMARY

A handheld rotary medical device with a shaver configured to remove cartilage is disclosed. The handheld rotary medical device may include an inner drive shaft and an elongated, tubular, outer housing encapsulating the inner drive shaft such that the inner drive shaft is positioned within the outer housing and a shaver at a distal end of the inner drive shaft. The shaver may include a plurality of teeth extending radially outward from an outer surface of the inner drive shaft. The medical device may include slots or grooves in the outer housing useful for cleaning the tissue from the teeth of the shaver.

In at least one embodiment, the handheld rotary medical device may be formed from an inner drive shaft and an elongated, tubular, outer housing encapsulating the inner drive shaft such that the inner drive shaft is positioned within the outer housing. The device may also include a shaver at a distal end of the inner drive shaft. The shaver may include a plurality of teeth extending radially outward from an outer surface of the inner drive shaft. The plurality of teeth may be aligned into circumferential rows. The teeth within a row may be offset circumferentially relative to teeth in an adjacent circumferential row. The outer housing may include an opening aligned with the shaver at the distal end of the inner drive shaft.

In at least one embodiment, the device may include circumferential slots formed in a sidewall forming the outer housing at an opening aligned with the shaver at the distal end of the inner drive shaft. The slots may extend in a circumferential direction from a longitudinally extending edge forming an edge of the opening in the outer housing. One or more slots may be aligned with a portion of a first row of teeth and a portion of a second row of teeth. A plurality of slots may be aligned with a portion of a row of teeth and a portion of an adjacent row of teeth. In at least one embodiment, all of the slots may be aligned with a portion of a row of teeth and a portion of an adjacent row of teeth. The outer housing may include a distal opening at a distal end of the outer housing, wherein the distal opening is in communication with the opening in the outer housing that is aligned with the shaver. One or more circumferential rows may include a plurality of radially extending teeth. In at least one embodiment, each circumferential row may include a plurality of radially extending teeth. One or more teeth may have a generally rectangular leading face facing a direction of rotation of the inner drive shaft. One or more teeth may also have any other appropriate configuration to cut joint cartilage.

In another embodiment, each circumferential row of teeth may be offset circumferentially in a same circumferential direction. Each circumferential row of teeth may be formed from at least a plurality of teeth. In another embodiment, each circumferential row of teeth may be formed from at least three teeth that are equally spaced circumferentially. One or more teeth may have a generally triangular cross-section tapering into an outer surface of the inner drive shaft moving in a circumferential direction opposite to a direction of rotation of the inner drive shaft. One or more teeth may be elongated such that a longitudinal length of the teeth in a circumferential direction is greater than a width of the teeth at the outer surface of the inner drive shaft in a linear direction aligned with a longitudinal axis of the inner drive shaft. A leading face of the tooth may be generally triangular with sloped sides extending from the outer surface of the inner drive shaft to a point that forms a ridge extending circumferentially and radially inward into the outer surface of the inner drive shaft.

The device may also be configured to include circumferential grooves formed in an inner surface of the outer housing. The circumferential grooves may extend circumferentially from a first edge of the opening in the outer housing to a second edge of the outer housing. The circumferential grooves may be aligned with the circumferential rows of teeth. One or more of the circumferential grooves is formed from V shaped grooves, where each groove is formed with two sides converging into contact together in the outer housing.

An advantage of the device is that the device may be disposable.

Another advantage of the device is that the device may be configured to efficiently and effectively remove joint cartilage during joint fusion.

Yet another advantage of the device is that the device may be used for arthroscopic, minimally invasive surgery, and open joint preparation.

Another advantage of the device is that the device may be created in different sizes between and including, but not limited to, 3 millimeters and 5.5 millimeters for different joints and may have, but are not limited to having, lengths between about 7 centimeters and 13 centimeters.

These and other embodiments are described in more detail below.

DETAILED DESCRIPTION OF THE FIGURES

Figure 1:
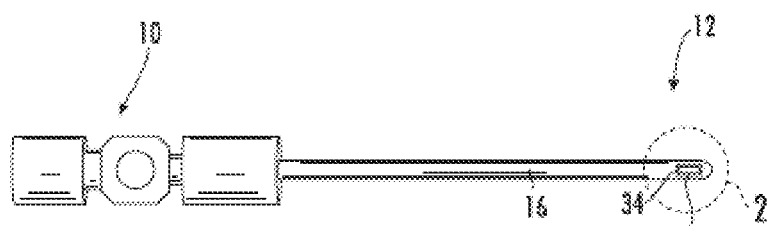
FIG. 1 is a perspective view of a handheld rotary medical device with a shaver.

As shown in FIGS. 1-5, a handheld rotary medical device 10 with a shaver 12 configured to remove cartilage is disclosed. The handheld rotary medical device 10 may include an inner drive shaft 14, an elongated, tubular, outer housing 16 encapsulating the inner drive shaft 14 such that the inner drive shaft 14 is positioned within the outer housing 16 and a shaver 12 at a distal end 20 of the inner drive shaft 14. The shaver 12 may include a plurality of teeth 22 extending radially outward from an outer surface 24 of the inner drive shaft 14. The medical device 10 may include slots 26 or grooves 28 in the outer housing 16 useful for cleaning the tissue from the teeth 22 of the shaver 12.

In at least one embodiment, the handheld rotary medical device 10 may include an inner drive shaft 14 and an elongated, tubular, outer housing 16 encapsulating the inner drive shaft 14 such that the inner drive shaft 14 is positioned within the outer housing 16. The inner drive shaft may be formed from any configuration capable of transferring rotary motion from a drive motor to the shaver 12. In at least one embodiment, the inner drive shaft 14 may be a cylindrical shaft. The inner drive shaft 14 may be a solid shaft or a tubular, hollow shaft. The outer housing 16 may be a hollow member with chamber 36 sized and configured to contain the inner drive shaft 14. The outer housing 16 may be a hollow tube or have another appropriate configuration. The inner drive shaft 14 and outer housing 16 may be formed from any appropriate material, such as, but not limited to, metal, such as stainless steel, titanium and other metals, plastics and other materials. The handheld rotary medical device 10 may or may not be disposable.

Figure 2:
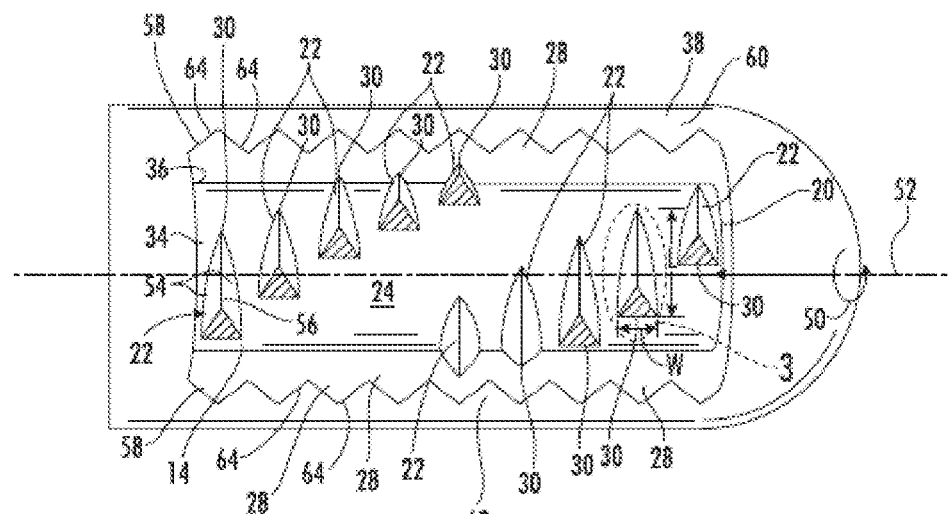
FIG. 2 is a detail top view of the shaver taken at detail 2 in FIG. 1.

The device 10 may include a shaver 12 at a distal end 20 of the inner drive shaft 14. The shaver 12 may include a plurality of teeth 22 extending radially outward from an outer surface 24 of the inner drive shaft 14. The plurality of teeth 22 may be aligned into circumferential rows 30. In at least one embodiment, teeth 22 within a row 30 may be offset circumferentially relative to teeth 22 in an adjacent circumferential row 30. In at least one embodiment, as shown in FIGS. 2, 4 and 5, the outer housing 16 may include an opening 34 aligned with the shaver 12 at the distal end 20 of the inner drive shaft 14.

Figure 3:
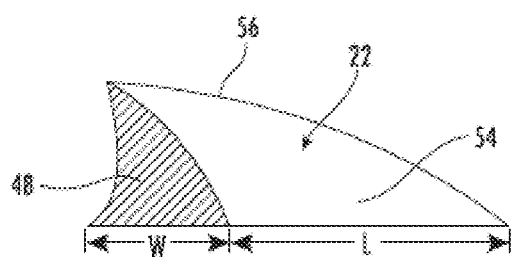
FIG. 3 is a detail side view of a tooth taken at detail 3 is FIG. 2.
Figure 4:
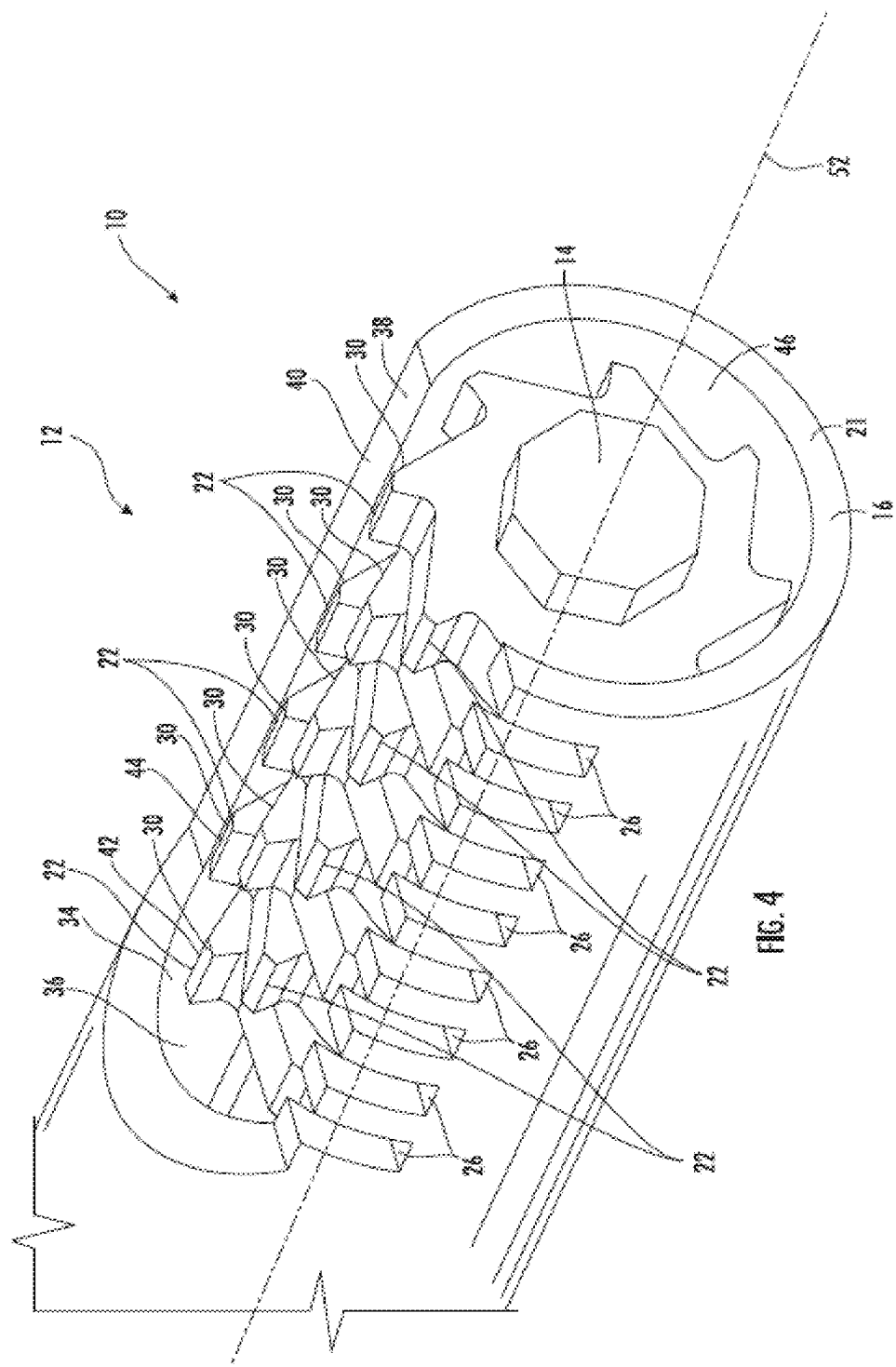
FIG. 4 is perspective view of another embodiment of the shaver.
Figure 5:
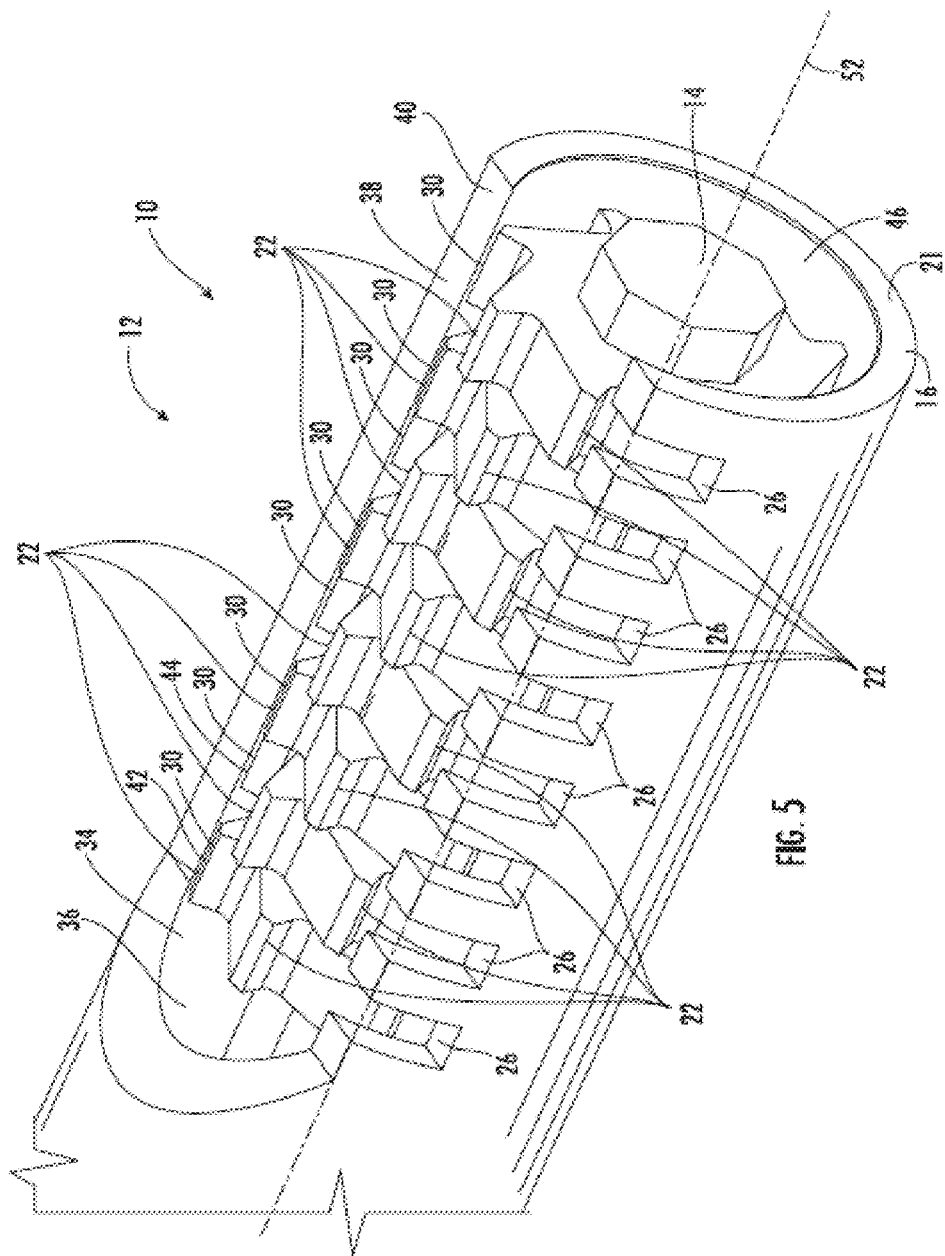
FIG. 5 is another perspective view of the shaver shown in FIG. 4.

As shown in FIGS. 4 and 5, the handheld rotary medical device 10 may include circumferential slots 26 formed in a sidewall 38 forming the outer housing 16 at the opening 34 aligned with the shaver 12 at the distal end 20 of the inner drive shaft 14, wherein the slots 26 may extend in a circumferential direction from a longitudinally extending edge 40 forming an edge 40 of the opening 34 in the outer housing 16. The slot 26 may be aligned with a portion of a first row of teeth 22 and a portion of a second row 44 of teeth 22. In embodiments with a plurality of teeth 22, the plurality of slots 26 are aligned with a portion of a row 30 of teeth 22 and a portion of an adjacent row of teeth 22. All of the plurality of slots 26 may be aligned with a portion of a row of teeth 22 and a portion of an adjacent row of teeth 22. The outer housing 16 may include a distal opening 46 at a distal end 21 of the outer housing 16. The distal opening 46 may be in communication with the opening 34 in the outer housing 16 that is aligned with the shaver 12. In at least one embodiment, at least one circumferential row 30 may include a plurality of radially extending teeth 22. In another embodiment, the device 10 may be configured such that each circumferential row 30 includes a plurality of radially extending teeth 22. As shown in FIGS. 2 and 3, the device 10 may include one or more teeth having a generally rectangular leading face 48 facing a direction of rotation 50 of the inner drive shaft 14.

In another embodiment, as shown in FIGS. 4 and 5, the device 10 may be configured with another configuration of teeth 22. In particular, the device 10 may include one or more teeth wherein each circumferential row 30 of teeth 22 are offset circumferentially in a same circumferential direction. In at least one embodiment, each circumferential row 30 of teeth 22 may be formed from at least a plurality of teeth 22. Each circumferential row 30 of teeth 22 may be formed from at least a three teeth 22. The teeth 22 may be equally spaced circumferentially or may be positioned at different distances from each other. As shown in FIGS. 2 and 3, one or more teeth 22 may have a generally triangular cross-section tapering into an outer surface 24 of the inner drive shaft 14 moving in a circumferential direction opposite to a direction of rotation of the inner drive shaft 14. One or more teeth 22 may be elongated such that a longitudinal length of the tooth 22 in a circumferential direction is greater than a width of the tooth 22 at the outer surface 24 of the inner drive shaft 14 in a linear direction aligned with a longitudinal axis 52 of the inner drive shaft 12. A leading face 48 of the tooth 22 is generally triangular with sloped sides 54 extending from the outer surface 24 of the inner drive shaft 14 to a point that forms a ridge 56 extending circumferentially and radially inward into the outer surface 24 of the inner drive shaft 14.

The device shown in FIGS. 4 and 5, may include circumferential grooves 28 formed in an inner surface 58 of the outer housing 16. The circumferential grooves 28 may extend circumferentially from a first edge 60 of the opening 34 in the outer housing 16 to a second edge 62 of the outer housing 16. The circumferential grooves 28 may be aligned with the circumferential rows 30 of teeth 22. One or more of the circumferential grooves 28 may be formed from V shaped grooves 28. The V shaped grooves 28 may be formed with two sides 64 converging into contact together in the outer housing 16.

During use the shaver 12 may be used to efficiently and effectively remove joint cartilage such as, but not limited to, during joint fusion. The shaver 12 may be used for arthroscopic, MIS, and open joint preparation. The shaver 12 may be used by a surgeon or other user to remove articular cartilage in preparation for fusion procedures. The shaver 12 may rotate in a single direction or may oscillate about a longitudinal axis 52 of the inner drive shaft 14. The shaver 12 catches, cuts and minces the cartilage into small pieces capable of being easily removed.

The foregoing is provided for purposes of illustrating, explaining, and describing embodiments of the disclosed devices.

We claim:
1. A method of preparing tissue, comprising:
placing a shaver of a handheld rotary medical device in contact with the tissue, wherein the handheld rotary medical device comprises:
an inner drive shaft;
an elongated, tubular, outer housing encapsulating the inner drive shaft such that the inner drive shaft is positioned within the outer housing;
the shaver at a distal end of the inner drive shaft, wherein the shaver includes a plurality of teeth extending radially outward from an outer surface of the inner drive shaft, wherein the plurality of teeth are aligned into circumferential rows and wherein teeth within a row are offset circumferentially relative to teeth in an adjacent circumferential row;
wherein the outer housing includes an opening aligned with the shaver at the distal end of the inner drive shaft; and
wherein at least one tooth has a generally triangular cross-section tapering into an outer surface of the inner drive shaft moving in a circumferential direction opposite to a direction of rotation of the inner drive shaft; and operating the handheld rotary medical device to cause the shaver to be rotated while in contact with the tissue.

2. The method of preparing tissue of claim 1, wherein operating the handheld rotary medical device comprises operating the handheld rotary medical device to cause the shaver to rotate in a single direction.

3. The method of preparing tissue of claim 1, wherein operating the handheld rotary medical device comprises operating the handheld rotary medical device to cause the shaver to oscillate.

4. The method of preparing tissue of claim 1, wherein the handheld rotary medical device further comprises circumferential slots formed in a sidewall forming the outer housing at the opening aligned with the shaver at the distal end of the inner drive shaft, wherein the slots extend in a circumferential direction from a longitudinally extending edge forming an edge of the opening in the outer housing.

5. The method of preparing tissue of claim 4, wherein at least one slot is aligned with a portion of a first row of teeth and a portion of a second row of teeth.

6. The method of preparing tissue of claim 5, wherein at least a plurality of the slots are aligned with a portion of a row of teeth and a portion of an adjacent row of teeth.

7. The method of preparing tissue of claim 6, wherein all of the plurality of the slots are aligned with a portion of a row of teeth and a portion of an adjacent row of teeth.

8. The method of preparing tissue of claim 1, wherein the outer housing includes a distal opening at a distal end of the outer housing, wherein the distal opening is in communication with the opening in the outer housing that is aligned with the shaver.

9. The method of preparing tissue of claim 1, wherein at least one circumferential row includes a plurality of radially extending teeth.

10. The method of preparing tissue of claim 9, wherein each circumferential row includes a plurality of radially extending teeth.

11. The method of preparing tissue of claim 1, wherein at least one tooth has a generally rectangular leading face facing a direction of rotation of the inner drive shaft.

12. The method of preparing tissue of claim 1, wherein each circumferential row of teeth are offset circumferentially in a same circumferential direction.

13. The method of preparing tissue of claim 12, wherein each circumferential row of teeth is formed from at least a plurality of teeth.

14. The method of preparing tissue of claim 13, wherein each circumferential row of teeth is formed from at least three teeth that are equally spaced circumferentially.

15. The method of preparing tissue of claim 12, further comprising circumferential grooves formed in an inner surface of the outer housing, wherein the circumferential grooves extend circumferentially from a first edge of the opening in the outer housing to a second edge of the outer housing, and wherein the circumferential grooves are aligned with the circumferential rows of teeth.

16. The method of preparing tissue of claim 15, wherein at least one of the circumferential grooves is formed from V shaped grooves, where each groove is formed with two sides converging into contact together in the outer housing.

17. The method of preparing tissue of claim 1, wherein at least one tooth is elongated such that a longitudinal length of the at least one tooth in a circumferential direction is greater than a width of the at least one tooth at the outer surface of the inner drive shaft in a linear direction aligned with a longitudinal axis of the inner drive shaft.

18. The method of preparing tissue of claim 17, wherein a leading face of the at least one tooth is generally triangular with sloped sides extending from the outer surface of the inner drive shaft to a point that forms a ridge extending circumferentially and radially inward into the outer surface of the inner drive shaft.

19. A method of preparing tissue, comprising:
placing a shaver of a handheld rotary medical device in contact with the tissue, wherein the handheld rotary medical device comprises:
an inner drive shaft;
an elongated, tubular, outer housing encapsulating the inner drive shaft such that the inner drive shaft is positioned within the outer housing;
the shaver at a distal end of the inner drive shaft, wherein the shaver includes a plurality of teeth extending radially outward from an outer surface of the inner drive shaft, wherein the plurality of teeth are aligned into circumferential rows and wherein teeth within a row are offset circumferentially relative to teeth in an adjacent circumferential row;
wherein the outer housing includes an opening aligned with the shaver at the distal end of the inner drive shaft;
circumferential slots formed in a sidewall forming the outer housing at the opening aligned with the shaver at the distal end of the inner drive shaft, wherein the slots extend in a circumferential direction from a longitudinally extending edge forming an edge of the opening in the outer housing;
wherein the outer housing includes a distal opening at a distal end of the outer housing, wherein the distal opening is in communication with the opening in the outer housing that is aligned with the shaver; and
wherein at least one slot of the circumferential slots is aligned with a portion of a first row of teeth and a portion of a second row of teeth; and
operating the handheld rotary medical device to cause the shaver to be rotated while in contact with the tissue.

20. A method of preparing tissue, comprising:
placing a shaver of a handheld rotary medical device in contact with the tissue, wherein the handheld rotary medical device comprises:
an inner drive shaft;
an elongated, tubular, outer housing encapsulating the inner drive shaft such that the inner drive shaft is positioned within the outer housing;
the shaver at a distal end of the inner drive shaft, wherein the shaver includes a plurality of teeth extending radially outward from an outer surface of the inner drive shaft, wherein the plurality of teeth are aligned into circumferential rows and wherein teeth within a row are offset circumferentially relative to teeth in an adjacent circumferential row;
wherein the outer housing includes an opening aligned with the shaver at the distal end of the inner drive shaft;
wherein at least one tooth has a generally rectangular leading face facing a direction of rotation of the inner drive shaft;
wherein each circumferential row of teeth are offset circumferentially in a same circumferential direction; and
circumferential grooves formed in an inner surface of the outer housing, wherein the circumferential grooves extend circumferentially from a first edge of the opening in the outer housing to a second edge of the outer housing, and wherein the circumferential grooves are aligned with the circumferential rows of teeth; and operating the handheld rotary medical device to cause the shaver to be rotated while in contact with the tissue.

\* \* \* \* \*